United States Patent [19]

Daoudal et al.

[11] Patent Number: 5,932,615

[45] Date of Patent: Aug. 3, 1999

[54] DISINFECTING COMPOSITION ESPECIALLY SUITABLE FOR THE TREATMENT OF LIVESTOCK BUILDINGS

[76] Inventors: José Daoudal, 39, rue Benoît Frachon; Frédéric Lucas, 16, passage de Compiégne, both of 53000 Laval, France

[21] Appl. No.: 08/949,346

[22] Filed: Oct. 14, 1997

[30] Foreign Application Priority Data

Oct. 16, 1996 [FR] France .................................. 96 12616

[51] Int. Cl.⁶ .................................................. A01N 53/00
[52] U.S. Cl. ............................................................. 514/531
[58] Field of Search ................................................ 514/531

[56] References Cited

U.S. PATENT DOCUMENTS

| 4,579,677 | 4/1986 | Hooper et al. | 252/95 |
| 5,397,795 | 3/1995 | Valcke | 514/383 |

FOREIGN PATENT DOCUMENTS

| 2 502 010 | 9/1983 | France . |
| 2 622 397 | 5/1989 | France . |
| 3636541 | 4/1988 | Germany . |
| 2 205 748 | 12/1988 | United Kingdom . |
| 2 211 414 | 7/1989 | United Kingdom . |
| WO 93/17558 | 9/1993 | WIPO . |

*Primary Examiner*—José G. Dees
*Assistant Examiner*—Alton Pryor
*Attorney, Agent, or Firm*—Baker & Daniels

[57] ABSTRACT

Disinfecting composition in aqueous solution especially suitable for the treatment of livestock buildings, characterised in that it comprises, by weight, from 1 to 20% of monoaldehydes or dialdehydes, especially glutaraldehyde, from 3 to 35% of salts, especially quaternary ammonium chlorides, from 1 to 15% of ethoxylated fatty alcohol and from 0.5 to 15% of an insecticidal agent selected from synthetic pyrethrinoids.

11 Claims, 4 Drawing Sheets

FIG. 1a
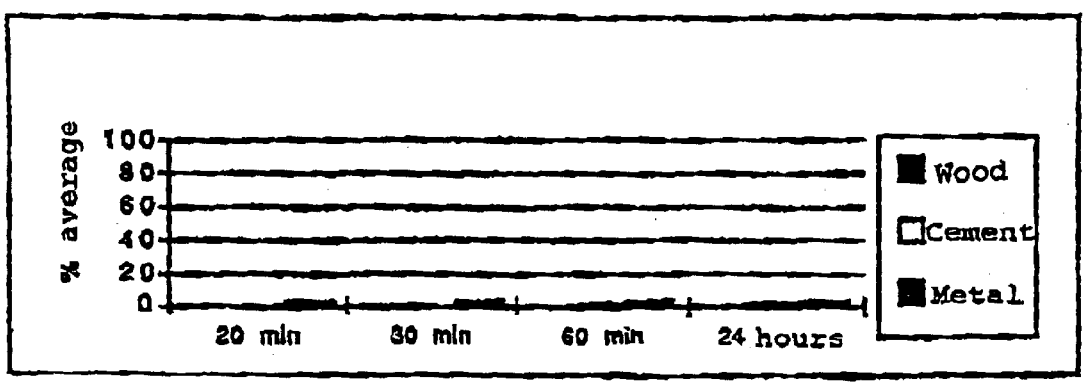
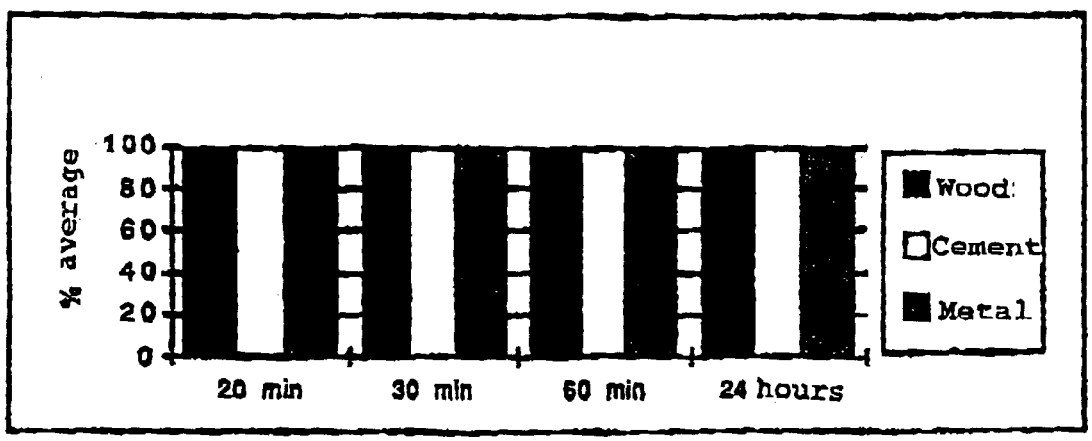
FIG. 1b

DISINFECTING COMPOSITION ESPECIALLY SUITABLE FOR THE TREATMENT OF LIVESTOCK BUILDINGS

BACKGROUND AND SUMMARY

The present invention relates to a disinfecting composition in aqueous solution especially suitable for the treatment of livestock buildings during the so-called "cleanout" periods which separate each group of animals.

There are currently a large number of disinfecting compositions on the market which are intended for the cleaning of buildings associated with industrial livestock rearing.

In order to be satisfactory, such compositions must of course have a pronounced disinfecting activity, that is to say, a bactericidal, virucidal and fungicidal action; they must also be chemically degradable or biodegradable, and they must be non-toxic and exhibit low corrosiveness.

In order to meet these various criteria, the publication FR-A-87 15 212 has already proposed a composition comprising, by weight, from 3 to 35% of quaternary ammonium salts, from 1 to 20% of straight-chain dialdehyde, especially glutaraldehyde, and from 1 to 15% of ethoxylated fatty alcohols.

In use, that composition has been found to be especially active, easy to eliminate, and to pose no danger to public health.

The bactericidal, virucidal and fungicidal qualities of quaternary ammonium compounds and glutaraldehyde have been well known for a long time.

In the above-mentioned disinfecting composition, the fatty alcohols act as wetting agents and solubilisers capable of improving the "stability" of the solution and permitting an increase in the proportion of active products.

The combination of quaternary ammonium salts, glutaraldehyde and ethoxylated fatty alcohols therefore makes it possible to obtain, in aqueous solution, very concentrated disinfecting compositions having a very broad spectrum of disinfecting activity and having, especially, a very pronounced virucidal activity owing to the excellent surfactant activity of the quaternary ammonium compounds.

By way of example, the following composition has been found to be especially active:

| | |
|---|---|
| Didecyldimethylammonium chloride | 18.75 g |
| Dioctyldimethylammonium chloride | 18.75 g |
| Octyldecyldimethylammonium chloride | 37.50 g |
| Alkyl (C14 50% - C12 40% - C16 10%) dimethylbenzylammonium chloride | 50 g |
| Glutaraldehyde | 62.50 g |
| Terpineol | 20 g |
| Pine oil | 20 g |
| Ethoxylated fatty alcohol having 10 moles of ethylene oxide and 90% of active substances | 40 g |
| Angelica green colorant (E 131 + E 104) | 1 g |
| Water q.s. | 1 litre |

Despite its undoubted advantage, this disinfecting composition has the disadvantage of having no insecticidal action and therefore of having to be combined with a supplementary treatment using an insecticidal product in order to obtain a complete sanitary "process".

Those operations constitute an economic and material constraint (number of operations, exposure of personnel, lengthening of "cleanout" periods in the livestock buildings, . . . ).

Consequently, and despite manufacturers' recommendations, users are sometimes tempted to mix, in the course of the same treatment, disinfecting agents having no insecticidal action and insecticidal agents having no bactericidal or virucidal power. The mixtures so produced, however, bring together substances which are not necessarily compatible with one another and may even cause poisoning accidents.

In addition, studies which enable manufacturers to determine the efficacy of their product do not take systematic account of the interactions which may occur when the products are associated with another agent and cannot ensure that the products so mixed preserve their activity and their chemical stability.

It would therefore be desirable to be able to provide a polyvalent agent that efficiently combines disinfecting (bactericidal, virucidal and fungicidal) properties with insecticidal properties.

Despite this apparent need, it has not been possible hitherto to combine the necessary active substances in a stable water-miscible form at suitable concentrations enabling the efficacy indispensable for a single useful dose to be obtained.

The object of the present invention is to fill this gap by proposing a composition suitable for the treatment of livestock buildings which is chemically stable while having a high degree of both insecticidal and bactericidal, virucidal and fungicidal efficacy and which is at the same time non-toxic in respect of the use for which it is intended and which exhibits low corrosiveness towards the materials exposed to it (especially metals).

BRIEF DESCRIPTION OF DRAWINGS

FIG. 1a is a graph illustrating the percentage mortalities obtained with flies on various untreated surfaces;

FIG. 1b is a graph illustrating the percentage mortalities obtained with flies on various surfaces after the surfaces are treated with a composition in accordance with the present invention;

DETAILED DESCRIPTION

Figure 2:
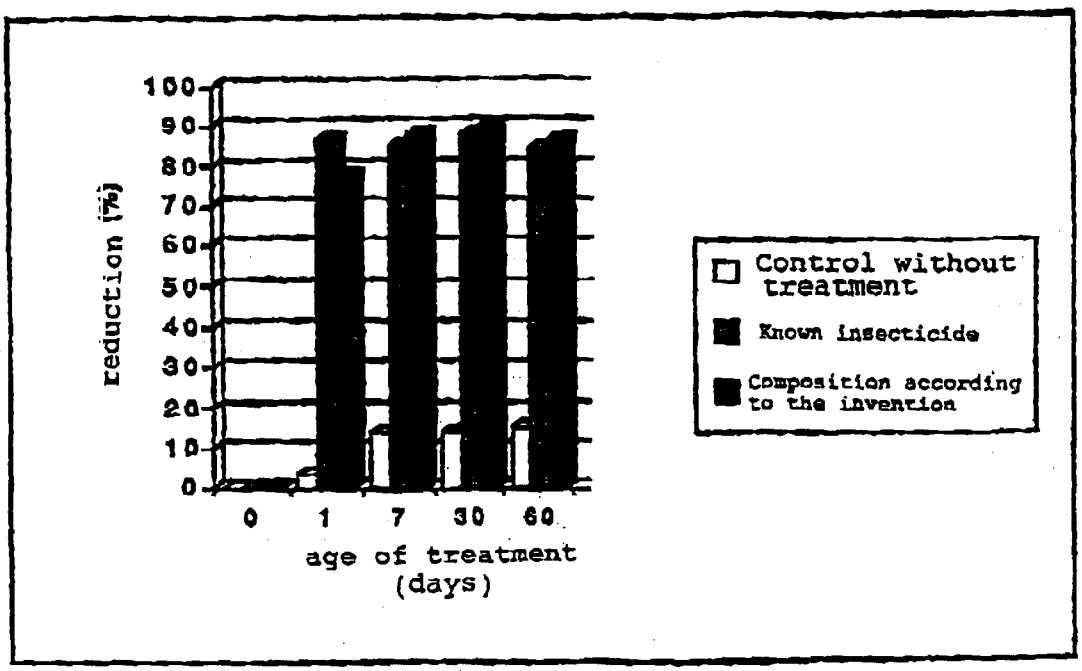
FIG. 2 is a graph illustrating the variation in fly population in livestock buildings over time on an untreated building, a building treated with a composition according to the present invention, and on a building treated with a known insecticide.

In accordance with the invention, the composition is characterized in that it comprises, by weight, from 1 to 20% of monoaldehydes or dialdehydes, especially glutaraldehyde, from 3 to 35% of salts, especially quaternary ammonium chlorides, from 1 to 15% of ethoxylated fatty alcohol and from 0.5 to 15% of an insecticidal agent selected from synthetic pyrethrinoids, that is to say, analogues of pyrethrin, which is an insecticide known per se formed by toxic constituents extracted from the flowers and the overground parts of pyrethrum (Chrysanthemum Cineraria Folium).

It has been surprisingly been realised that it is possible, by starting from the above-mentioned known disinfecting composition forming the subject matter of document FR-A-87 15 212 and by adjusting the nature and proportions of the solvents and surfactants used, to obtain a stable and efficient polyvalent composition by dint of the incorporation of a particular insecticidal agent.

In accordance with the invention, that insecticidal agent may advantageously be constituted by an isomer or a mixture of isomers of permethrin, especially a mixture of approximately 25% of cis isomer and approximately 75% of trans isomer.

Permethrin or 3-phenoxybenzyl (1, RS)-cis,trans-3-(2,2-dichlorovinyl)-2,2-dimethylcyclopropane carboxylate is a pyrethrinoid which has a broad spectrum of activity and which is distinguished by good persistence and the efficacy of which permits insecticidal protection when it is used at a low dose.

The composition according to the invention may advantageously comprise approximately 20 g of synthetic pyrethrinoids and especially of permethrin per liter of solution.

According to a further feature of the invention, the composition comprises from 0.2 to 40% of terpene extract and especially of terpineol.

The addition of terpineol to the composition according to the invention is especially advantageous bearing in mind the fact that that compound, which has notable bactericidal qualities, at the same time acts as a perfume.

By way of example, 100 g of terpineol may be used per liter of solution.

According to another feature of the invention, the composition basically comprises, per liter of solution, 60 g of ethoxylated fatty alcohols, constituted by ethoxylated compounds having 11 moles of ethylene oxide, and 45% of active substance.

Those fatty alcohols act as wetting agents and solubilisers.

Advantageously, it is also possible to use, as quaternary ammonium salts, salts broadly similar to those included in the above-mentioned disinfecting composition forming the subject matter of document FR-A-87 15 212, namely dialkyldimethylammonium chlorides and/or alkylbenzyldimethylammonium chlorides of which the alkyl radicals comprise from 8 to 16 carbon atoms.

According to another feature of the invention, the composition basically comprises, per liter of solution, 125 g of quaternary ammonium salt constituted by a mixture of didecyldimethylammonium chloride, dioctyldimethylammonium chloride, octyldecyldimethylammonium chloride and alkyldimethylbenzylammonium chlorides, the latter being constituted by a mixture of approximately 50% by weight of C14 compounds, 40% by weight of C12 compounds and 10% by weight of C16 compounds.

According to a further feature of the invention, the composition basically comprises 62.5 g of glutaraldehyde per liter of solution.

The composition according to the invention may, of course, comprise other additives, such as, for example, a colorant, especially a green colorant.

By way of example, the following composition has been found to be especially advantageous in use:

| | |
|---|---|
| Didecyldimethylammonium chloride | 18.75 g |
| Dioctyldimethylammonium chloride | 18.75 g |
| Octyldecyldimethylammonium chloride | 37.50 g |
| Alkyldimethylbenzylammonium chloride | 50 g |
| (Alkyl: C14 50% - C12 40% - C16 10%) | |
| Glutaraldehyde | 62.50 g |
| Permethrin (cis/trans isomer: 25%/75%) | 20 g |
| Ethoxylated fatty alcohol having | 60 g |
| 11 moles of ethylene oxide and 45% of | |
| active substances | 60 g |
| Terpineol | 100 g |
| Angelica green colorant (E131 - E104) | 0.020 g |
| Demineralised water q.s. | 1 litre |

The properties of the composition forming the subject matter of the invention have been demonstrated by the experimental tests described below:

1) Insecticidal efficacy

Two tests were carried out in order to evaluate the insecticidal power of the composition according to the invention. The use of such tests proved to be indispensable bearing in mind the fact that, although the insecticidal properties of pyrethrinoids are well known per se, it did not automatically follow that there was no risk of the occurrence, within the composition, of an antagonist or of a phenomenon of the active substances' being "trapped" by the other constituents.

a) Trial carried out in the laboratory

This test was carried out in accordance with the "Protocole expérimental destiné à établir, en laboratoire, l'efficacité d'une spécialité insecticide" (Experimental protocol for determining, in the laboratory, the efficacy of an insecticidal agent) (Centre National d'Etudes Vétérinaires et Alimentaires) (National Centre for Veterinary and Food Studies) and demonstrated the efficacy of treatment with the composition according to the invention on different kinds of surface (wood, cement and metal). The results, which give the percentage mortalities obtained with flies, are compiled in FIG. 1a (corresponding to mortality without treatment) and in FIG. 1b (corresponding to mortality after treatment).

From the first 20 minutes of exposure, efficacy is optimum.

b) Trials carried out in situ

Only natural conditions of use enable the real efficacy of an insecticide to be evaluated. The remanence of treatment is an important criterion for this type of product. Remanence is influenced by the stability and the persistence of the insecticide on surfaces inasmuch as the insecticide acts by contact with the insect. Contact with the insect is itself influenced by the natural fouling of livestock buildings in the course of time.

The trial was carried out in accordance with method No. 107: "Méthode d'essai d'efficacité pratique de produits insecticides destinés à lutter contre les mouches des étables dans les locaux d'élevages d'animaux domestiques" (Practical efficacy trial method for insecticidal products that are to combat stable flies in buildings for rearing domestic animals) established by the members of the Commission des Essais Biologiques de l'Association Nationale pour la Protection des Plantes (Biological Trial Commission of the National Association for the Protection of Plants). Carried out in the summer, the trial consisted in comparing the variations in the fly population in livestock buildings in the course of the 3 months following the treatment.

The trial was carried out on an untreated building, on a building treated with the composition according to the invention and on a building treated with a known insecticide, in this case used as a positive control.

The results obtained are indicated in FIG. 2.

Conclusion:

The results show that the composition according to the invention is as efficient as a known exclusively insecticidal product.

2) Bactericidal and virucidal efficacy

Bactericide

Preliminary tests demonstrated that the active substances responsible for bactericidal activity preserve their power. The synergistic association of the mixture of quaternary ammonium compounds and aldehydes in the prior art disinfecting composition according to document FR-A-87 15 212 is not inhibited in the composition according to the invention. This check was carried out by comparing the MBC (minimum bactericidal concentrations) obtained on the strain Pseudomonas acruginosa in the presence of hard water at 30° F. (method: by microplates according to AFNOR NF T 72–170). Four variants of the composition according to the invention were tested (the variations concerned the ratios of surfactants and co-solvents).

Results:

For each trial (including prior art disinfecting composition), the Minimum Bactericidal Concentrations are obtained for dilutions lower than or equal to 0.125%.

Conclusion:

Bactericidal efficacy is maintained compared with the prior art disinfecting composition which is authorised for use at a dilution of 0.5% on the Pseudomonas strain aeruginosa; the use of the composition according to the invention is intended for a dilution of 2%.

b) Virucide

The preliminary trial was carried out by micromethod on the virus of Talfan's disease (type 1 picornavirus) which is well known for its resistance to disinfectants, which resistance therefore constitutes the limiting factor for the usable dilution.

Results:

The composition according to the invention, diluted to 2%, leads to a fall of at least 3 Log in the viral content, in conformity with the requirements of the Laboratoire des Médicaments Vétérinaires (Laboratory of Veterinary Medicaments) regarding disinfectants for agricultural use.

3) Chemical stability

The stability study carried out on the composition comprises a check on the appearance of the product, measurement of the pH and the content of the active substances. The study is carried out on samples stored in polypropylene bottles in an oven at 37° C. in order to obtain an accelerated ageing profile.

The data below correspond to groups stored at 37° C. for more than 3 months.

a) Appearance of the samples

Absence of precipitates No phase separation of the constituents Stable colouring In other words, appearance unchanged after 3 months at 37° C.

b) Stability of the aldehydes

Figure 3:
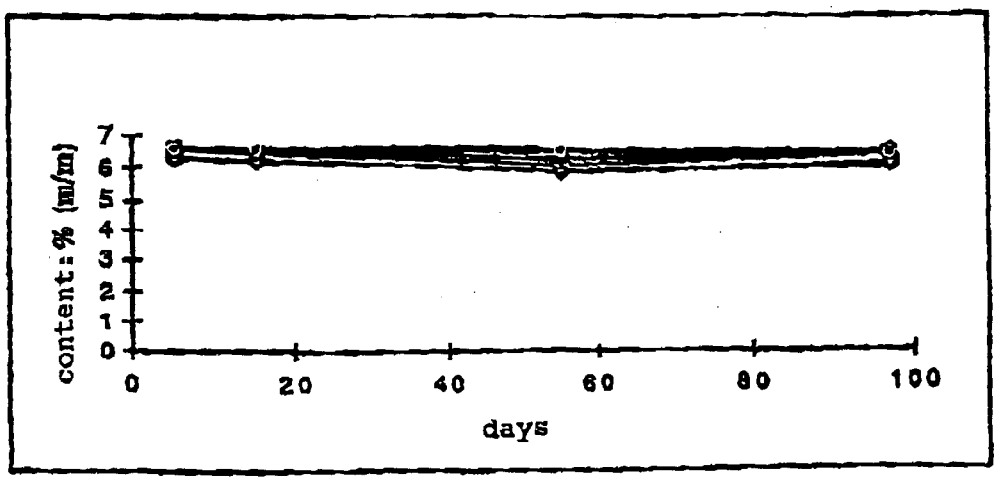
FIG. 3 is a graph illustrating the stability of the composition in accordance with the present invention, particularly the aldehyde component thereof.

The stability at 37° C. of the aldehyde is represented in FIG. 3.

No significant degradation after 99 days at 37° C.

c) Stability of the quaternary ammonium compounds

Figure 4:
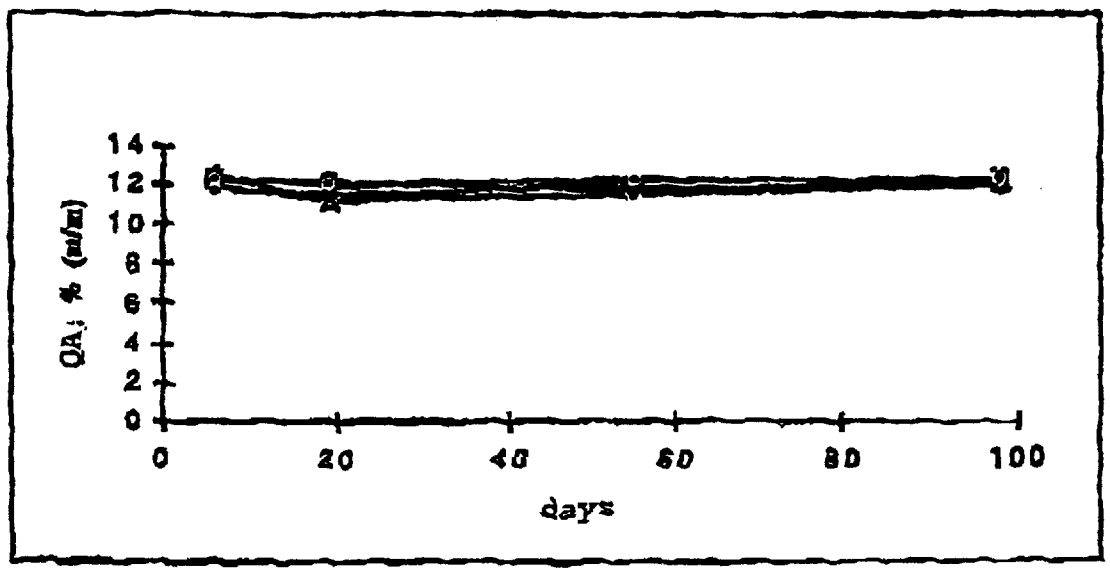
FIG. 4 is a graph illustrating the stability of the composition in accordance with the present invention, particularly the quaternary ammonium compound portion thereof.

The stability at 37° C. of the quaternary ammonium compounds is represented in FIG. 4.

NO significant degradation after 99 days at 37° C.

d) Stability of permethrin

Figure 5:
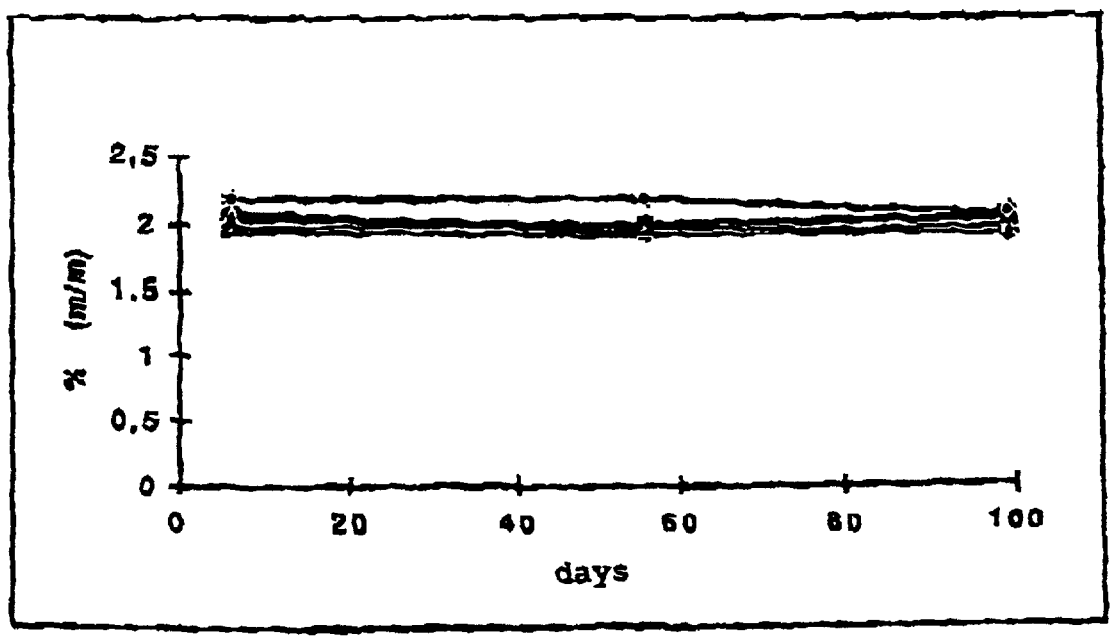
FIG. 5 is a graph illustrating the stability of the composition in accordance with the present invention, particularly the permethrin component thereof.

The stability at 37° C. of permethrin is represented in FIG. 5.

No significant degradation after 99 days at 37° C.

e) Variations in the pH

Figure 6:
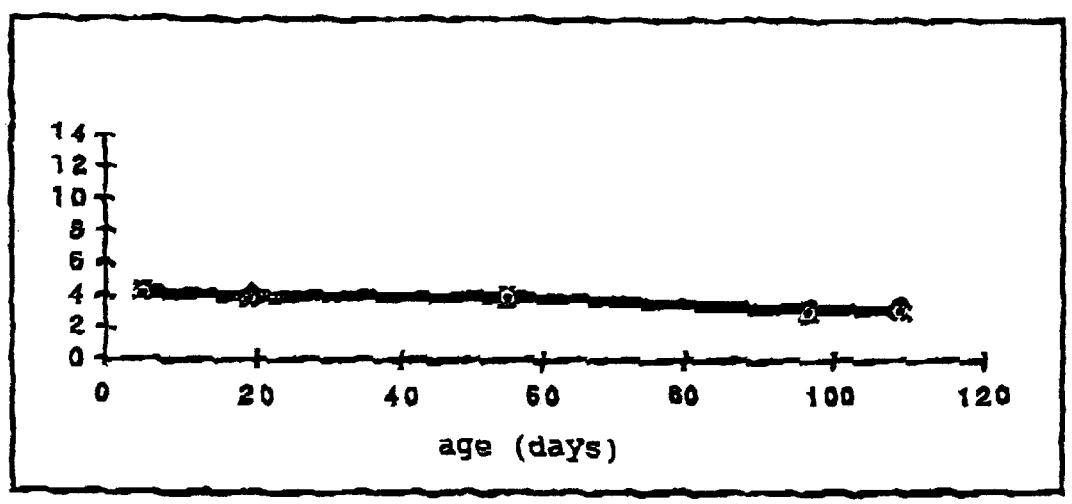
FIG. 6 is a graph illustrating the stability of the composition in accordance with the present invention, particularly the pH thereof.

The evolution of the pH at 37° C. is represented in FIG. 6.

The pH decreases slightly after two months.

f) Observations

The graphs below correspond to the results of quantitative analyses carried out on six different batches of the composition according to the invention. There is some variation between the batches in respect of the percentages of excipients.

It will be noted that the active substances exhibit satisfactory resistance to the ageing conditions at 37° C. for at least three months.

4) Toxicological aspect

The various constituents of the composition according to the invention do not present any particular danger at the useful dose provided for (2% in aqueous dilution).

5) Corrosiveness of the composition

At the useful doses, the composition does not present any particular risk to the materials exposed to the treatments.

We claim:

1. A disinfecting composition for use in the treatment of livestock buildings, said composition comprising an aqueous solution by weight:

from 1 to 20% of one of a monoaldehyde and a dialdehyde;

from 3 to 35% of quaternary ammonium chlorides;

from 1 to 15% of ethoxylated fatty alcohols; and from 0.5 to 15% of a synthetic pyrethroid insecticidal agent.

2. The composition of claim 1, wherein the insecticidal agent is one of an isomer and a mixture of isomers of permethrin.

3. The composition of claim 2, wherein the insecticidal agent comprises approximately 25% of cis isomer and 75% of trans isomer.

4. The composition of claim 1, further comprising from 0.2 to 40% of terpene extract.

5. The composition of claim 1, wherein the quaternary ammonium chlorides are selected from the group consisting of dialkyldimethylammonium chlorides and alkylbenzyldimethylammonium chlorides, the quaternary ammonium chlorides of the group having alkyl radicals comprising from 8 to 16 carbon atoms.

6. The composition of claim 5, comprising, per liter of solution, 125 g of quaternary ammonium chloride which further comprises a mixture of didecyldimethyl-ammonium chloride, dioctyldimethylammonium chloride, octyldecyldimethylammonium chloride and alkyldimethylbenzylammonium chloride, the latter comprising a mixture of approximately 50% by weight of C14 compounds, 40% by weight of C12 compounds and 10% by weight of C16 compounds.

7. The composition of claim 1, wherein the 1 to 20% of one of a monoaldehyde and a dialdehyde comprises glutaraldehyde.

8. The composition of claim 1, wherein said synthetic pyrethroid comprises about 20 g of permethrin per liter of solution.

9. The composition of claim 1, wherein said ethoxylated fatty alcohol has a concentration of about 60 g per liter of solution, said ethoxylated fatty alcohol comprising ethoxylated compounds having 11 moles of ethylene oxide, and 45% of active substance.

10. The composition of claim 1, further comprising about 100 g of terpineol per liter of solution.

11. A disinfecting composition in aqueous solution, suitable for the treatment of livestock buildings, said composition comprising by weight;

from 1 to 20% of glutaraldehyde;

from 3 to 35% of at least one substance selected from the group consisting of dialkyldimethylammonium chlorides and alkylbenzyldimethylammonium chlorides, the alkyl radicals of said substance comprising from 8 to 16 carbon atoms;

from 1 to 15% of ethoxylated fatty alcohols comprising ethoxylated compounds having 11 moles of ethylene oxide and 45% of active substance;

from 0.5 to 15% of a synthetic pyrethroid insecticidal agent; and the composition being free from salts of hydroxy-containing aliphatic or aromatic acids.

* * * * *